(12) United States Patent
Sauer

(10) Patent No.: US 12,426,802 B2
(45) Date of Patent: Sep. 30, 2025

(54) SURGICAL SIZER SOUND

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 1046 days.

(21) Appl. No.: 17/344,153

(22) Filed: Jun. 10, 2021

(65) Prior Publication Data
US 2021/0386324 A1 Dec. 16, 2021

Related U.S. Application Data

(60) Provisional application No. 63/037,911, filed on Jun. 11, 2020.

(51) Int. Cl.
*A61B 5/107* (2006.01)
*A61B 90/00* (2016.01)

(52) U.S. Cl.
CPC ............ *A61B 5/1076* (2013.01); *A61B 90/03* (2016.02); *A61B 90/06* (2016.02); *A61B 2090/033* (2016.02)

(58) Field of Classification Search
CPC ....... A61B 5/1076; A61B 5/107; A61B 90/03; A61B 90/06; A61B 2090/033; A61B 2090/061; A61B 5/435; A61B 5/6865; A61B 90/10; A61B 2090/101–103; A61F 2/2496; A61F 2/2466; A61F 2/2427
See application file for complete search history.

(56) References Cited

U.S. PATENT DOCUMENTS

| | | | |
|---|---|---|---|
| 5,682,906 A | 11/1997 | Sterman et al. | |
| 5,713,951 A | 2/1998 | Garrison et al. | |
| 5,972,030 A * | 10/1999 | Garrison | A61B 17/06061 623/2.11 |
| 6,019,739 A | 2/2000 | Rhee et al. | |
| 2006/0282162 A1* | 12/2006 | Nguyen | A61F 2/2448 623/2.11 |
| 2007/0016287 A1* | 1/2007 | Cartledge | A61F 2/2448 623/2.37 |
| 2009/0192604 A1* | 7/2009 | Gloss | A61F 2/2496 623/2.11 |
| 2015/0012086 A1 | 1/2015 | Bassin | |
| 2020/0237510 A1* | 7/2020 | Carlino | A61B 5/1076 |

FOREIGN PATENT DOCUMENTS

WO 96/039942 12/1996

OTHER PUBLICATIONS

International Search Report and Written Opinion mailed Oct. 6, 2021, for International Application No. PCT/US21/36798, filed Jun. 10, 2021.
Extended European Search Report dated May 14, 2024, Application No. 21822457.4, 8 pages.

\* cited by examiner

*Primary Examiner* — Tse W Chen
*Assistant Examiner* — Evelyn Grace Park
(74) *Attorney, Agent, or Firm* — Michael E. Coyne

(57) ABSTRACT

A surgical sizer sound, comprising an actuatable shaft. The surgical sizer sound also comprises an angled shaft coupled to the actuatable shaft. The surgical sizer sound also comprises a sizer coupler comprising a guide tip and a limit, pivotably coupled to the angled shaft and a sizer, removably coupled to the sizer coupler.

12 Claims, 9 Drawing Sheets

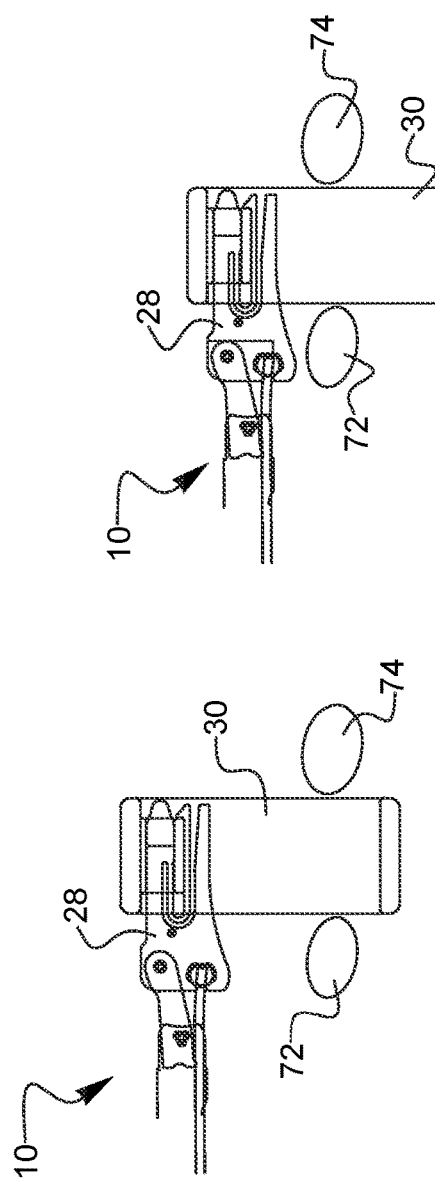
FIG. 7A
FIG. 7B
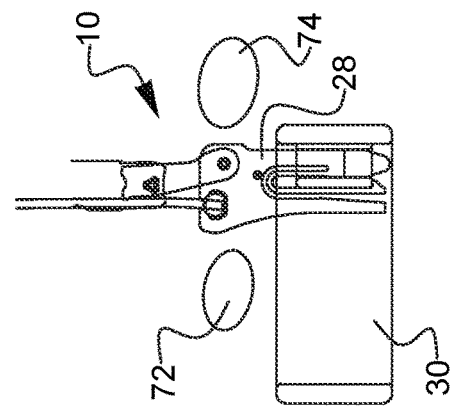
FIG. 7E
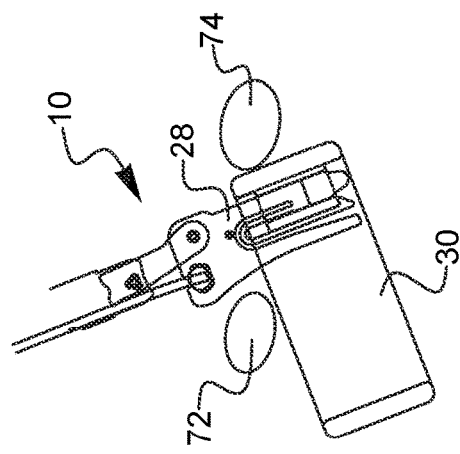
FIG. 7D
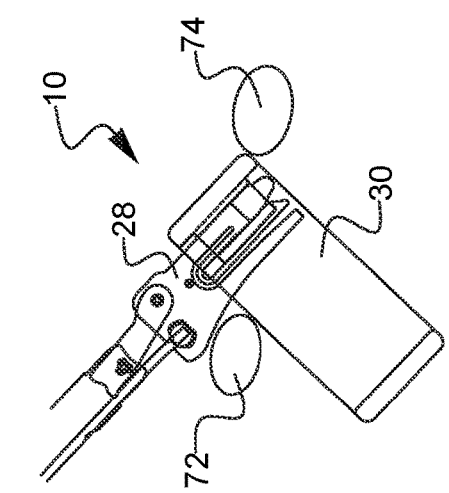
FIG. 7C

SURGICAL SIZER SOUND

RELATED APPLICATIONS

This application claims priority to U.S. Provisional Patent Application No. 63/037,911, which was filed on Jun. 11, 2020 and entitled "SURGICAL SIZER SOUND," the contents of which is hereby incorporated by reference in its entirety.

FIELD

The claimed invention relates to surgical sizing devices, and more specifically to a surgical sizer sound.

BACKGROUND

Modern advances in cardiac surgery have made it possible to replace heart valves using minimally invasive surgical techniques. As minimally invasive techniques have improved, surgeons are able to operate on patients through smaller and smaller access holes, resulting in less perioperative pain and shorter recovery times. A main focus of innovations in minimally invasive cardiac surgery has been on the tools which pass into the patient, through the small access holes, and ensuring these surgical tools and devices can be effectively used within the dimensions of a smaller access hole. By focusing on improvements to these elements of the surgical procedures, patients are able to be on cardiopulmonary bypass machines for shorter times, thereby improving patient outcomes. Resultant efficiency improvements while working within the patient further help to reduce stress and fatigue on surgeons.

If one or more of a person's heart valves developing problems which adversely affect their function can, consequently, it can negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve prolapses (extends back) into the left atrium during a ventricular contraction. Stenosis, by contrast, is when a heart valve does not fully patent due to stiff or fused leaflets, blood flow tract narrowing, or obstructive material buildup (e.g., calcium). The resultant narrowed outflow causes the heart to work harder to pump blood through it, possibly leading to heart failure.

Recent advances in cardiac surgery, and in particular the continuing reliability of cardio-pulmonary bypass (CPB) methods and instrumentation, have enabled less-invasive methods for heart valve replacement. Depending on the number of valves being replaced for a patient, a typical heart valve replacement surgery can last between two to six hours, one to two hours of which can be spent on a CPB machine. While the patient is on CPB, the surgeon must gain access to the heart valve, remove the pathologic valve tissue as necessary, and install a replacement valve at the location of the original valve. The valve installation process can be very time consuming, especially when surgeons are operating through small access sites when employing less-invasive techniques to reduce surgical trauma. Therefore, there is a need for devices and methods which enable surgeons to operate more efficiently during surgery to replace pathologic anatomical structures, such as, but not limited to, replacement heart valves. Such devices and methods can reduce the amount of time patients need to be attached to a CPB machine, thereby reducing the likelihood of CPB-related side effects. Devices and methods enabling surgeons to operate more effectively while utilizing smaller access sites to a surgical site may further result in benefits to the patient in terms of decreased pain, improved cosmetics, reduced hospital stays, and accelerated recovery.

BRIEF DESCRIPTION OF THE DRAWINGS

FIGS. 7A-7E are side, partial cross-sectional views of the surgical sizer sound of FIG. 1 during a surgical procedure introducing the surgical sizer sound between two ribs.

Figure 1:
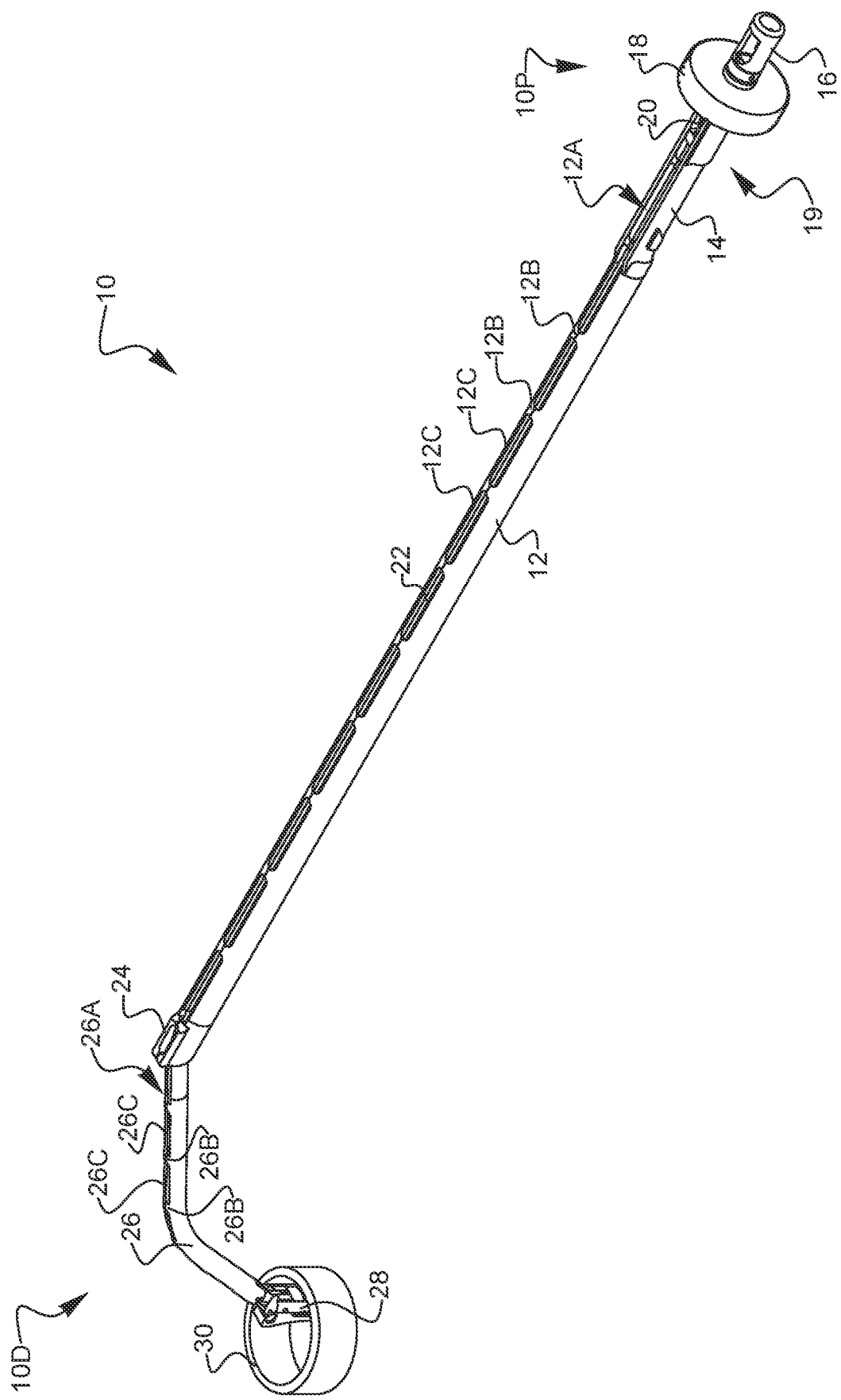
FIG. 1 is a top front left perspective view of a surgical sizer sound.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a top front left perspective view of a surgical sizer sound. An articulating, angled sizer sound as illustrated may be used in a minimally invasive coronary valve replacement surgical procedure. The sound 10, as described, is may be provided as a sterile, cleanable, and reusable product that is used to probe and couple to various coronary structures. The sound 10 is centrally comprised of a substantially cylindrical guide shaft 12, which towards a distal end 10D is coupled to an angled shaft mount 24 which is further coupled to an angled shaft 26. A sizer coupler 28 is pivotably coupled to the angled shaft 26, and a sizer 30 is removably coupled to the sizer coupler 28. A handle 14 is coupled to the guide shaft 12, and a rotating knob 18 and an end cap 16 are disposed at a proximal end 10P of the sound 10. A clockwise rotation 19 of the rotational knob 18 of the sound 10 will cause a drive screw 20 and attached drive wire 22, to retract and induce a pulling force on the drive wire 22 housed within the sizer coupler 28 on the distal end 10D of the sound 10. This pulling will cause the sizer coupler 28, and therefore the attached sizer 30, to follow rotation direction 70, pivoting about a pivot point, and move perpendicular to the angled shaft 26. Conversely rotating the rotational knob 18 in the opposite direction will impart a pushing force on the drive screw 20 and also the drive wire 22, causing the sizer coupler 28 to move in opposite direction 68 to return to its original position relative to the angled shaft 26. The full range of motion in the illustrated embodiment is approximately 90 degrees, although alternate embodiments may have a range of motion more than 90 degrees or may pivot in more than one direction relative to the angled shaft 26. Alternatively, using a reverse threaded rotatable knob 18 could provide for opposite actuation between the perpendicular and aligned positions. Alternate embodiments having an actuatable shaft distal end may incorporate an alternate operating mechanism such as a lever, slider, or other means known to those skilled in the art. As described previously, the drive screw 20 is engaged with the rotational knob 18 to push or pull the drive wire 22 which engages with and directs the sizer coupler 28. The drive wire 22 emanating from the drive screw 20 is delivered through the guide shaft 12 via a wire channel 12A, where it is retained by retaining tabs 12B and allowed cleaning access via cleaning troughs 12C. Lastly, the wire also passes through the angled shaft 26 via a wire channel 26A, where it is retained by retaining tabs 26B and allowed cleaning access via cleaning troughs 26C. At the distal end of the wire channel 26A, the wire 22 connects to the sizer coupler 28. Alternate embodiments may have shafts that are actuatable by means other than a rotational knob and drive screw, and may incorporate other operational or actuatable shafts by means such as levers, sliders, or other mechanical means known to those skilled in the art.

Figure 2:
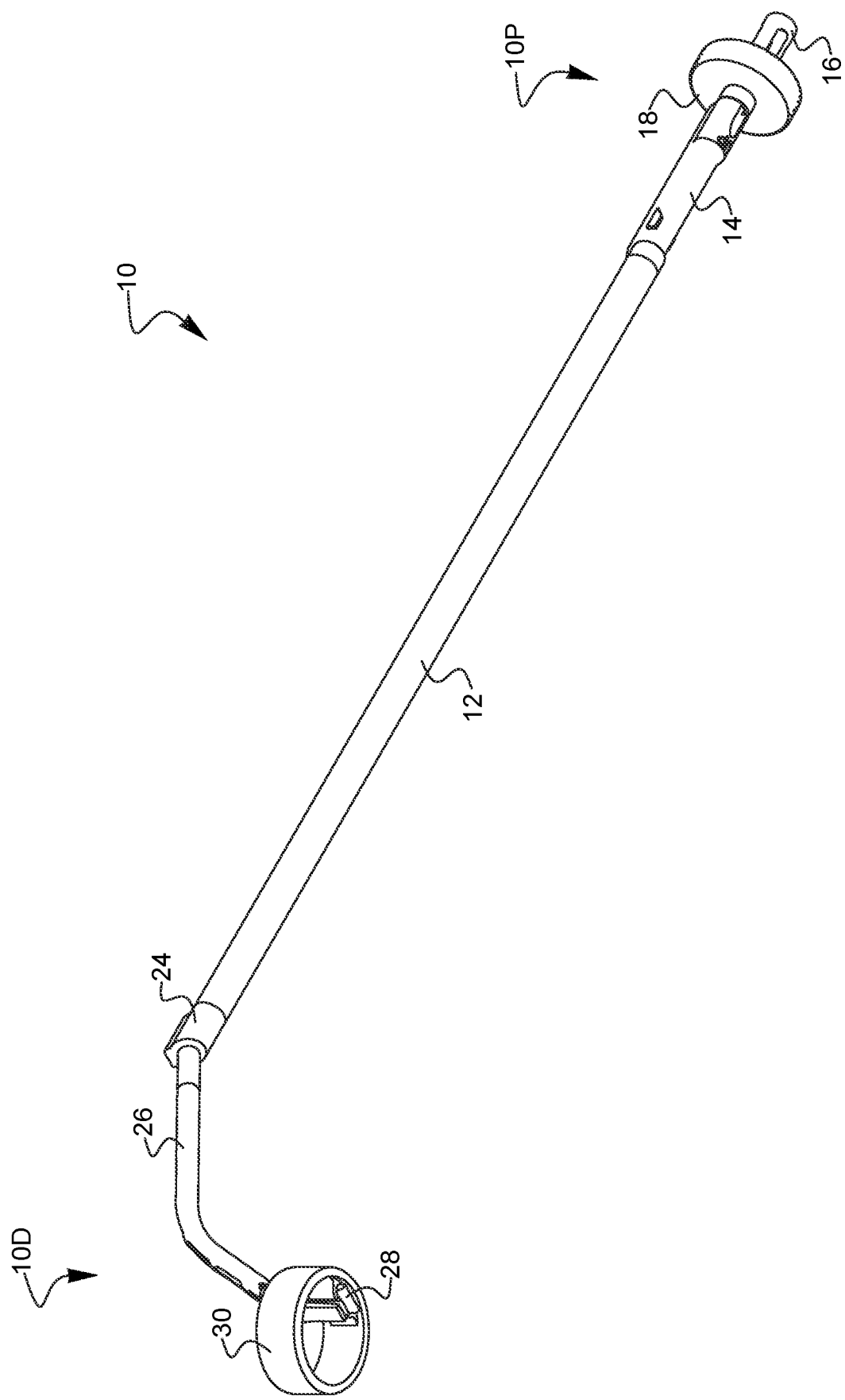
FIG. 2. is a bottom front left perspective view of the surgical sizer sound of FIG. 1.

It should be noted that due to variations in the human anatomy, different sizes of devices or individual components therein may be required from one surgical case to the next and the size of a heart and each annulus must be measured prior to selecting the appropriate size of a heart valve replacement. The sound 10 can be manufactured and offered with a variety of angled shafts 26 to accommodate an array of anatomical differences. Further, multiple dimensions relative to the sizer 30 may be provided depending on these anatomical variations from patient to patient. For example, a complement of six sizers having outer diameters of 19, 21, 23, 25, 27 and 29 mm in a surgical procedure kit may be provided. Alternatively, additional sizers in even increments such as 20 mm, 22 mm, or others may also be provided. Additional considerations may be addressed when a minimally invasive valve replacement valve replacement via microthoracotomy procedure is performed, such as angle of approach, dimensions of the sizer loaded onto the distal end, adjustability, and maneuverability. Alternate embodiments may include further articulation or angling points on the angled shaft 26 or incorporate a flexible or bendable angled shaft for setting and resetting a specific angle or profile on the angled shaft 26 relative to the guide shaft 12. The sound and related components described are manufactured from a non-corrosive, biocompatible, rigid, and sterilizable material, such as stainless steel. The sizer 30 may alternately be fabricated as a non-reusable component and from a biocompatible yet somewhat compressible or compliant material. Similar sounds used in minimally invasive surgical procedures and the assembly and associated methods thereof have been disclosed in U.S. Pat. No. 8,603,105 and in U.S. Pat. No. 10,092,323 both of which are hereby incorporated by reference in their entirety. FIG. 2. is a bottom front left perspective view of the surgical sizer sound of FIG. 1.

Figure 3A:
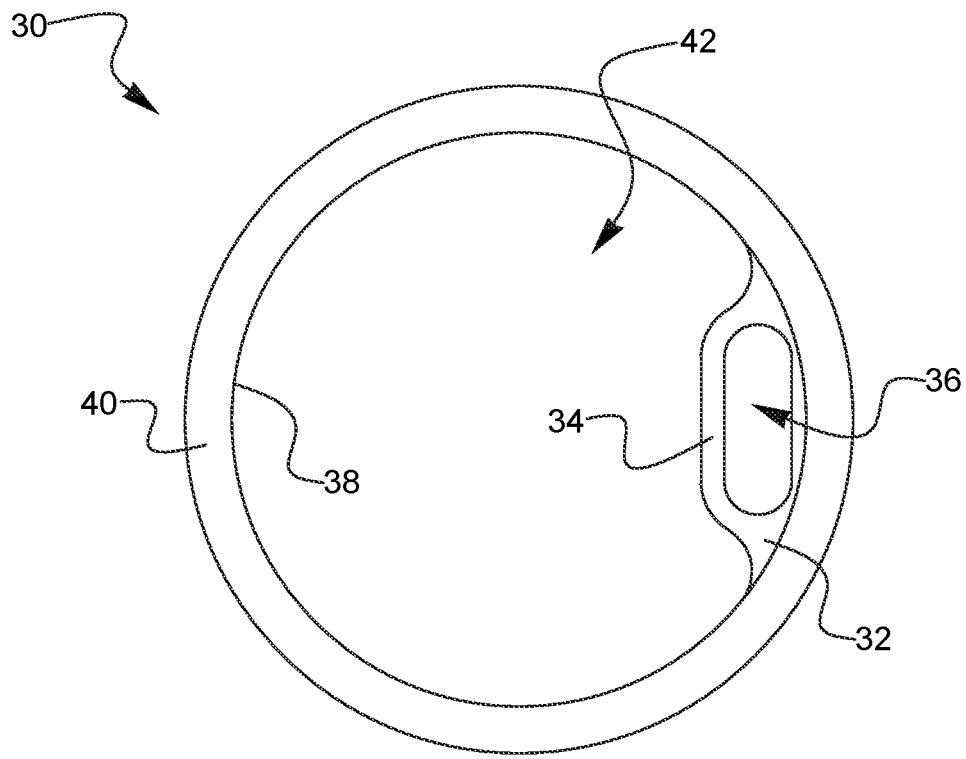
FIGS. 3A and 3B are a top view and a perspective view, respectively, of a sizer of the surgical sizer sound of FIG. 1.
Figure 3B:
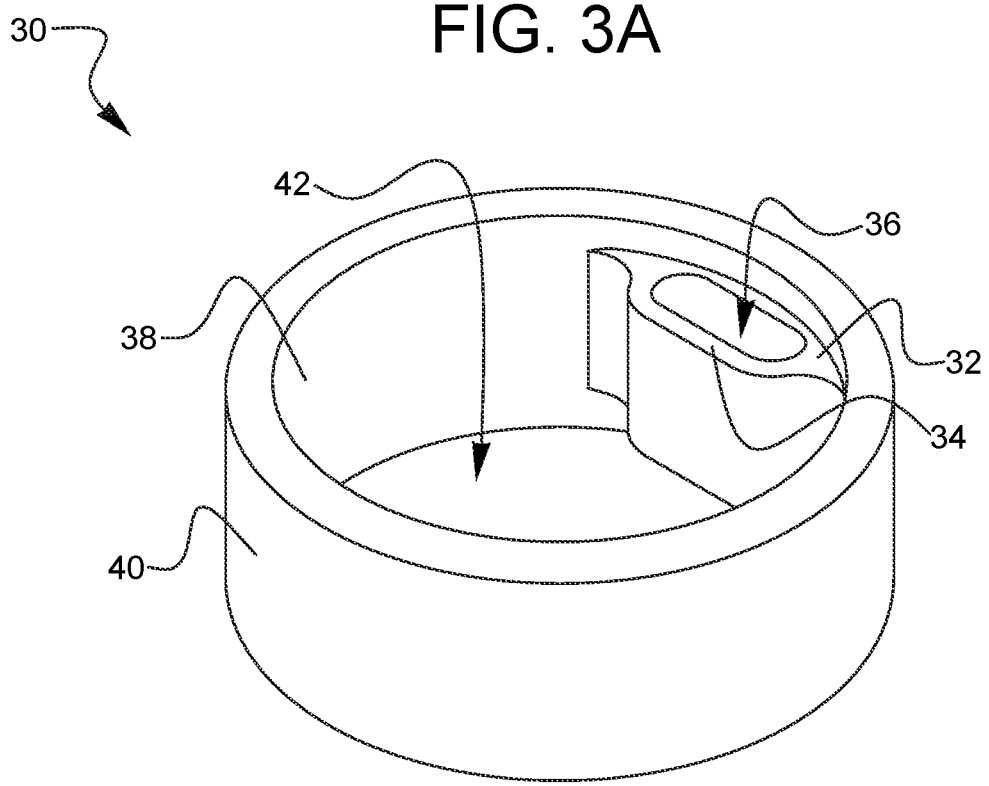

FIGS. 3A and 3B are a top view and a perspective view, respectively, of a sizer of the surgical sizer sound of FIG. 1. FIG. 3A is a top view of a sizer for use in the surgical sizer sound 10 of FIG. 1. The sizer 30 is comprised of a single component as a substantially hollow cylinder. The sizer 30 defines a mounting feature 32 on an inner circumference or inner wall 38 that defines an interior aperture 42, the mounting feature 32 having a sizer catch 34 and further defining a sizer mount opening 36. The sizer mount opening 36 is configured such that it corresponds to the dimensions and orientation of several features on the sizer coupler 28, which will be described in more detail later. The sizer 30 also defines an outer wall 40 located on the outer circumference of the sizer 30. The outer diameter defined by the outer wall 40 of the sizer 30 determine the size of the sizer 30 used in conjunction with the sizer sound 10 as releasably attached to the sizer coupler 28 during a minimally invasive cardiac valve replacement procedure. While the sizer 30 illustrated in FIGS. 3A and 3B is comprised of a single component, alternative embodiments may include a sizer with a mounting feature 32 that is fixedly attached or otherwise coupled to the inner circumference of the sizer 30. The mounting feature 32 is configured to engage and allow the sizer 30 to be releasably held the onto the sizer coupler 28 in a single, intended orientation. FIG. 3B is a perspective view of the sizer of FIG. 3A.

Figure 4A:
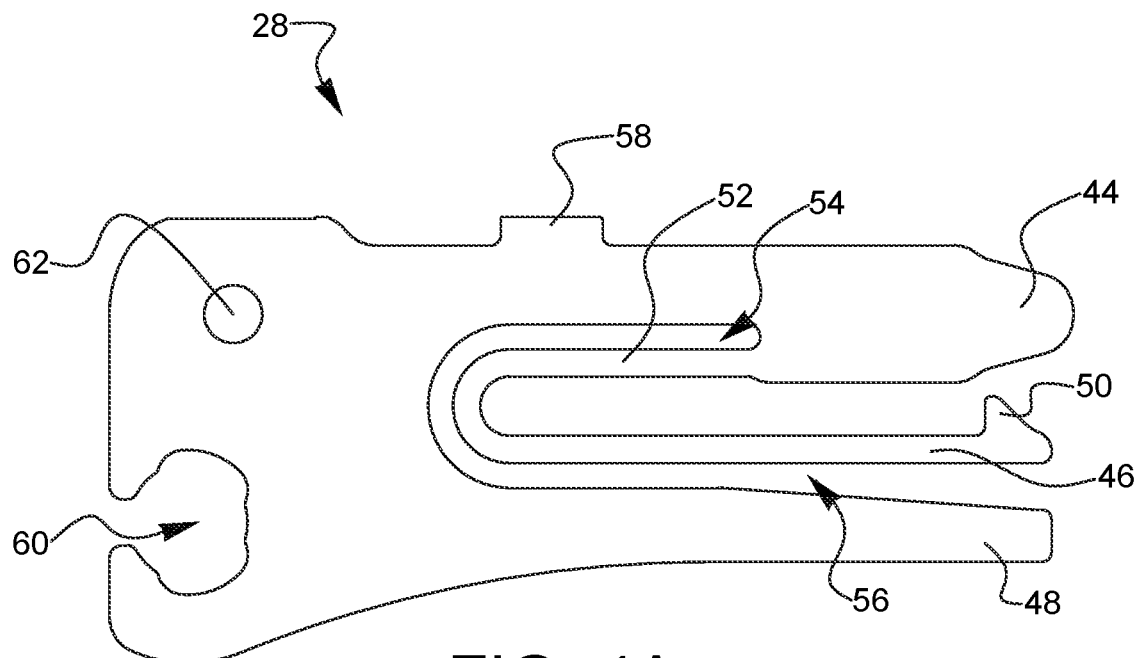
FIGS. 4A and 4B are left side and perspective views, respectively, of a sizer coupler of the surgical sizer sound of FIG. 1.
Figure 4B:
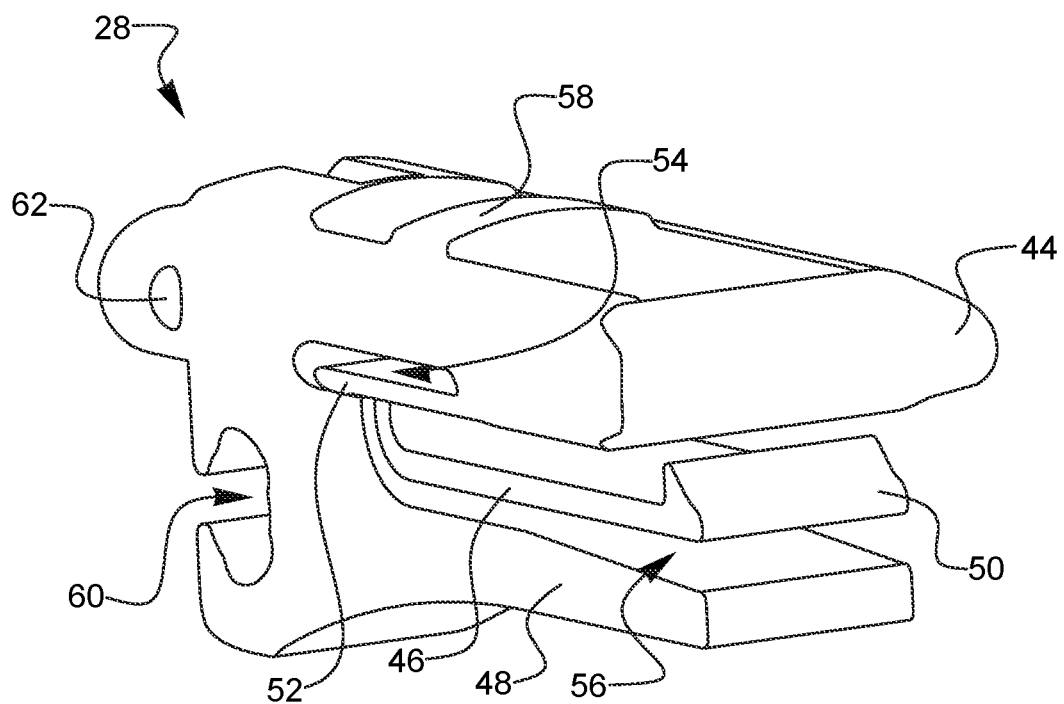

FIGS. 4A and 4B are left side and perspective views, respectively, of a sizer coupler of the surgical sizer sound of FIG. 1. The sizer coupler 28 a pivot point 62 and an actuator coupler 60 on one end. The actuator coupler 60 is configured to receive the drive wire 22 and is pivotably actuated about its pivot point 62 when the rotational knob 18 is actuated or rotated as described previously. Further details will be described in regard to FIG. 5B. The sizer coupler 28 also defines a guide tip 44, which is shaped and configured to interface with, receive, and release the sizer 30 during loading, use and unloading of the sizer sound 10 during a minimally invasive microthoracotomy involving a valve replacement procedure. The end of the guide tip 44 is rounded in order to facilitate the insertion of the guide tip 44 into a corresponding feature on the sizer 30. The guide tip 44 further defines a stop 58 which is a substantially rectangular-shaped protrusion configured to prevent a sizer from being inserted too far onto the guide tip 44. On the opposite side of the sizer coupler 28, the sizer coupler 28 further defines a limit 48. The limit 48 is coupled to the guide tip 44 by an internally curvilinear bridge. The guide tip 44 also includes a retainer 46 coupled to the guide tip 44 by a biasing element 52, the retainer 46 terminating in a latch 50 on its distal end. The guide tip 44, retainer 46, and limit 48 are substantially parallel and configured to receive a sizer 30 in a single orientation while preventing or reducing the possibility of loading a sizer 30 onto the sizer coupler 28 in an improper orientation. Between the guide tip 44 and the element 52 portion of the retainer 46, the sizer coupler 28 defines a first inner clearance gap. Between the limit 48 and the retainer 46, the sizer coupler 28 defines a second inner clearance gap 56. The biasing element 52 and retainer 46 have some flexibility such that the retainer 46 may flex towards the limit 48 to allow for the insertion of a sizer 30 onto the sizer coupler 28 between the guide tip 44 and retainer 46. The retainer 46 may also flex towards the limit 48 but cannot flex beyond the location of the limit 48, thus limiting the travel of the retainer 46 in a direction towards the limit 48 and away from the guide tip 44. The presence of the limit 48 on the sizer coupler 28 prevents the retainer 46 from becoming excessively flexed and potentially maintaining a flexed position after repeated use. While the sizer coupler shown is a singular piece, alternate embodiments may be comprised of separate components or multiple pieces assembled together.

Figure 5A:
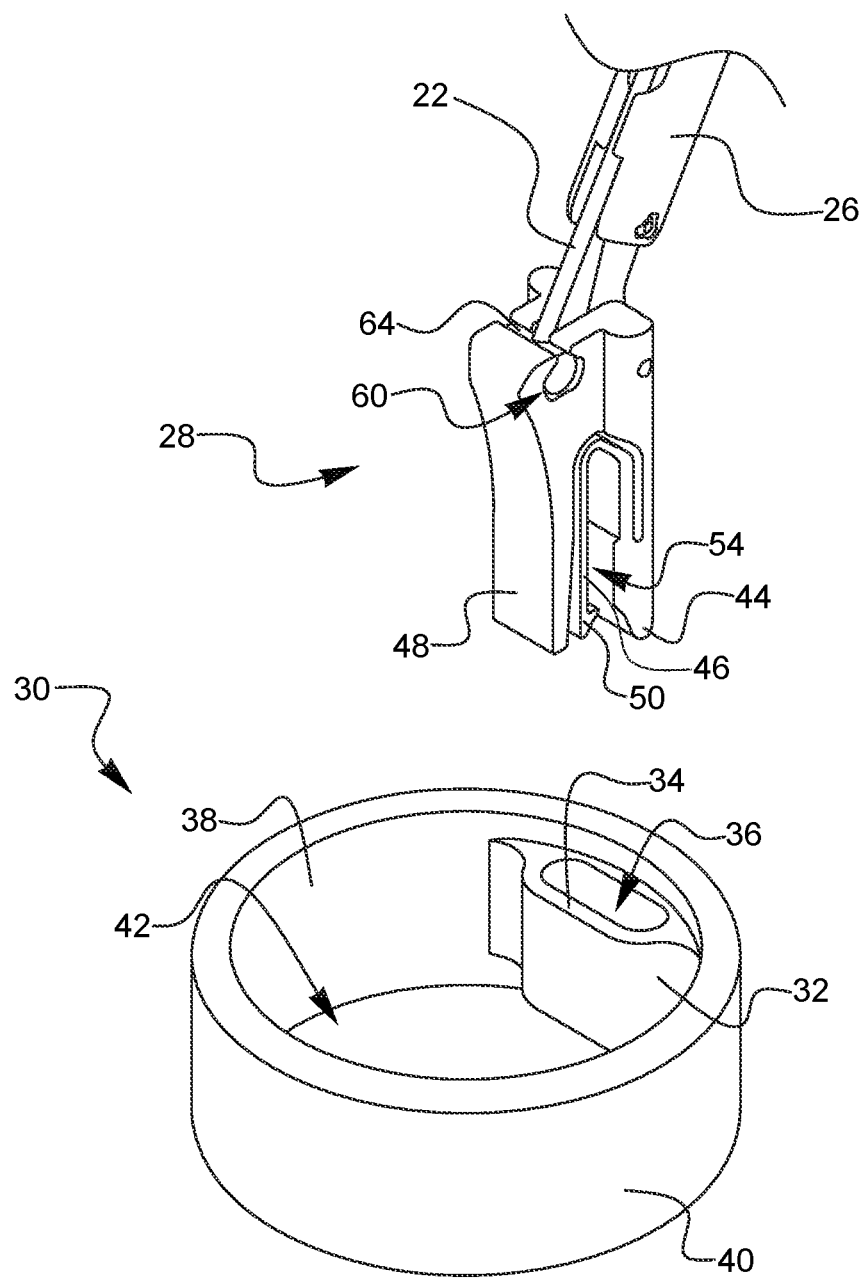
FIG. 5A is a perspective view of the sizer being loaded onto the sizer coupler.
Figure 5B:
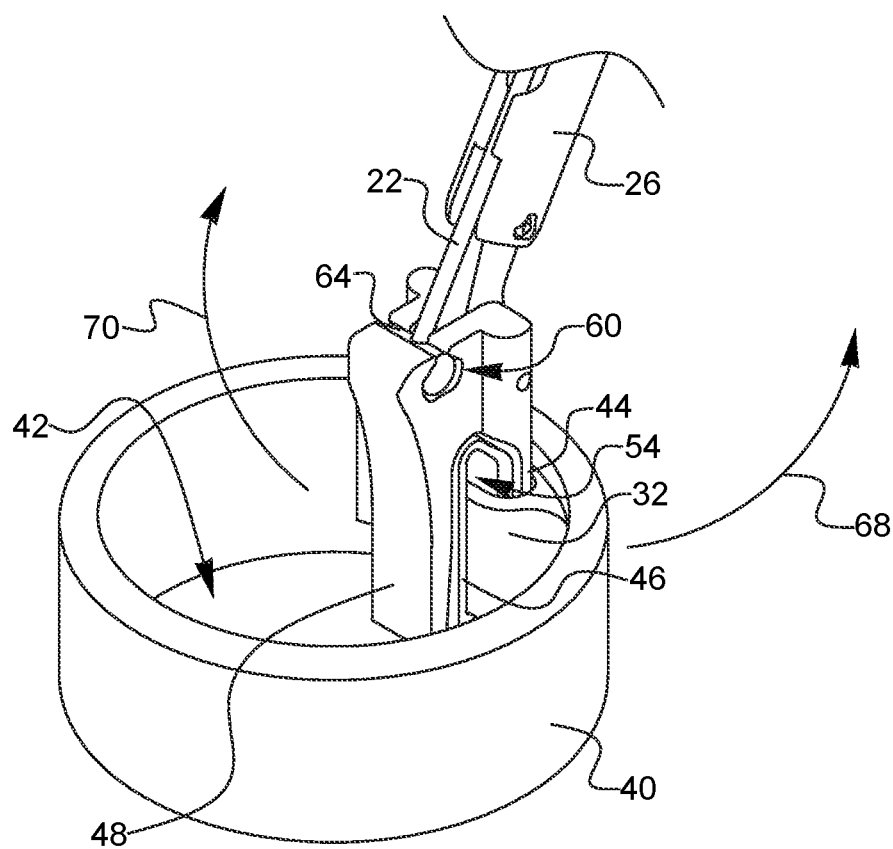
FIG. 5B is a perspective view of the sizer attached to the sizer coupler, illustrating the range of motion of the sizer coupler of the surgical sizer sound of FIG. 1.

FIG. 5A is a perspective view of the sizer being loaded onto the sizer coupler. FIG. 5A illustrates the appropriate positioning of the sizer 30 while being loaded onto the sizer coupler 28 of the sizer sound 10. This view of the distal end 10D of the sizer sound 10 illustrates the detail of the terminating drive wire coupler 64 as seated into the actuator coupler 60 of the sizer coupler 28. The complementary shape and orientation of the guide tip 44, retainer 46, and limit 48 on the sizer coupler 28 are oriented such that the guide tip 44 enters the sizer mount opening 36 on the sizer 30, the ramp-like shape of the latch 50 on the retainer 46 rides up and over the internal side of the sizer catch 34. The limit 48 prevents the retainer 46 from excessively flexing until the latch 50 clicks into place onto the edge of the sizer catch 34. This temporarily locks the sizer 30 onto the end of the sizer coupler 28 until such time that the latch 50 can be intentionally defeated to release the latch 50 and retainer 46 from the sizer catch 34 and allow removal of the sizer 30 from the sizer coupler 28. This fully loaded and locked configuration is illustrated in FIG. 5B. The described latch 50 defeat operation may be accomplished with the use of surgical tools such as graspers or other tools suitable for extension into a surgical port along with the sizer sound 10. FIG. 5B is a perspective view of the sizer attached to the sizer coupler, illustrating the range of motion of the sizer coupler of the surgical sizer sound of FIG. 1. As previously described, when the rotational knob 18 is rotated in a clockwise direction 19, the drive screw 20 and attached drive wire 22, are retracted and induce a pulling force on the drive wire 22 held within the actuator coupler 60 on the sizer coupler 28 on the distal end 10D of the sound 10. This pulling will cause the sizer coupler 28, and therefore the attached sizer 30, to follow rotation direction 70, pivoting about a pivot point 62, and move perpendicular to the angled shaft 26. Conversely rotating the rotational knob 18 in the opposite direction will impart a pushing force on the drive screw 20 and also the drive wire 22, causing the sizer coupler 28 to move in opposite direction 68 to return to its original position relative to the angled shaft 26 as illustrated in FIG. 5B.

Figure 6B:
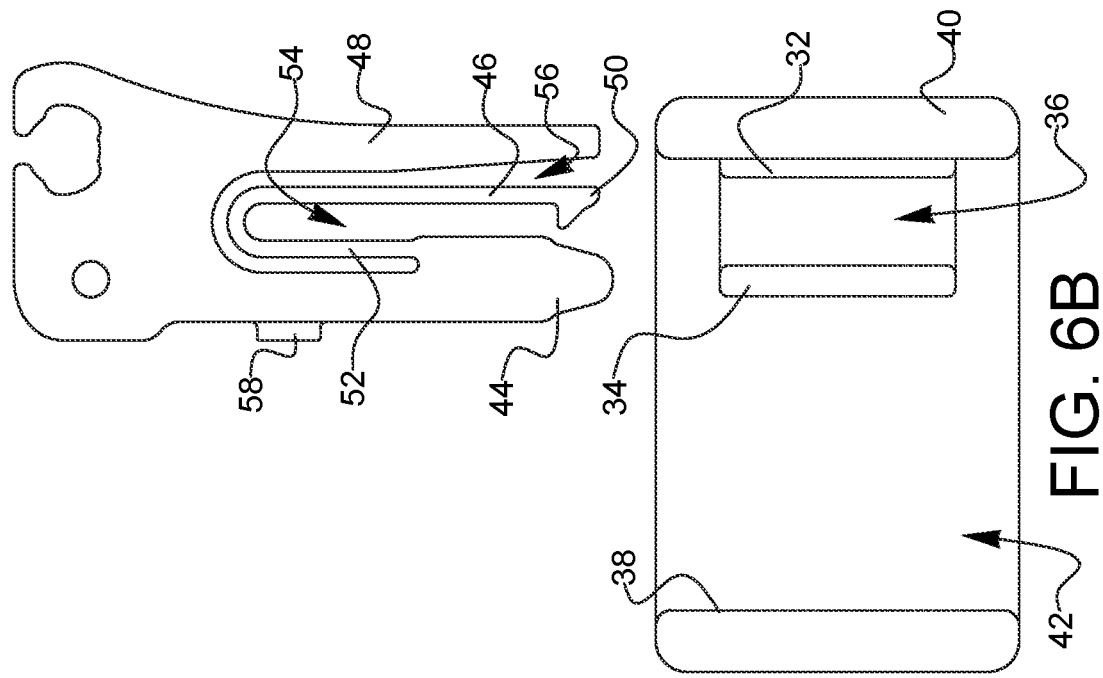
FIGS. 6A and 6B are partial cross-sectional views illustrating various loading positions of the sizer onto the sizer coupler of the of the surgical sizer sound of FIG. 1.
Figure 6A:
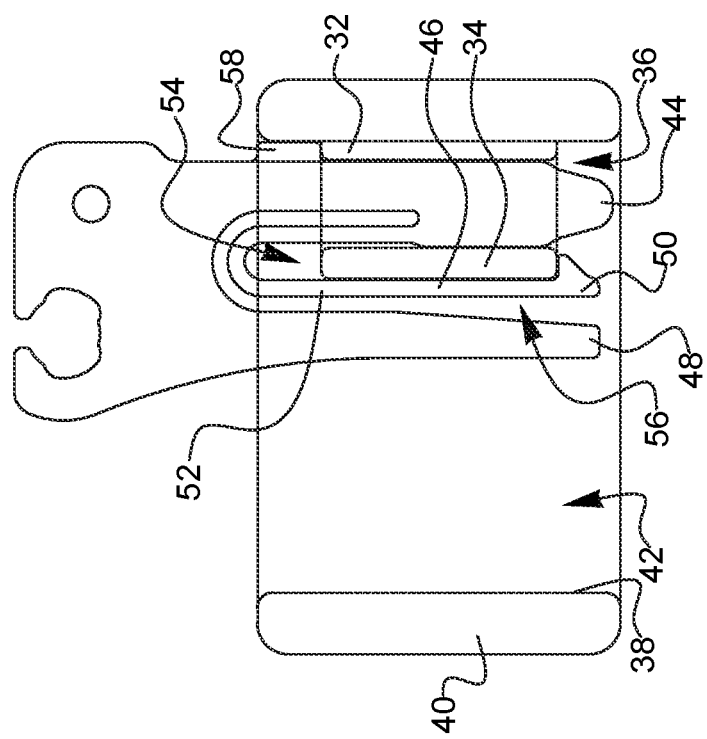

FIGS. 6A and 6B are partial cross-sectional views illustrating various loading positions of the sizer onto the sizer coupler of the of the surgical sizer sound of FIG. 1. FIG. 6A illustrates an appropriate loading orientation of the sizer 30 onto the sizer coupler 28. Several features of the sizer sound 10 are removed in FIGS. 6A and 6B for the purposes of clarity. The shape of the guide tip 44 is configured to fit into the sizer mount opening 36 of the sizer 30. The retainer 46 and limit 48 are configured to encourage insertion of the guide tip 44 of the sizer coupler 28 into the sizer mount opening 36 of the mounting feature 32 of the sizer 30 in only the orientation shown in FIG. 6A. The limit 48 prevents the retainer 46 from excessively flexing on the biasing element 52 attached to the guide tip 44 until the latch 50 of the retainer 46 clicks into place onto the edge of the sizer catch 34 once the guide tip 44 is fully inserted into the sizer mount opening 36 of the sizer 30. The retainer 46 may flex and travel through the second inner clearance gap 56 until the retainer 46 contacts the limit 48. Once the latch 50 has clicked into place on the edge of the sizer catch 34, the sizer catch 34 is seated within the first inner clearance gap 54 between the retainer 46 and the guide tip 44. The sizer coupler 28 and guide tip 44 are prevented from being further inserted into the sizer mount opening 36 by interference between the mounting feature 32 and the stop 58. Later removal of the sizer 30 from the sizer coupler 28 can be accomplished by mechanically defeating the latch 50 by pushing the latch 50 and retainer 46 through the second inner clearance gap 56 towards the limit 48 to clear the latch 50 from its holding position on the sizer catch 34 of the mounting feature 32 on the sizer 30. FIG. 6B shows an opposite orientation and positioning of the sizer coupler 28 being inserted into the sizer 30. While the guide tip 44 would fit into the sizer mount opening 36 of the mounting feature 32 on the sizer 30, the locations, position and configuration of the first inner clearance gap 54, retainer 46, second inner clearance gap 56, and limit 48 would impede or prohibit the insertion of the guide tip 44 on the sizer coupler 28 into the sizer mount opening 36 of the mounting feature 32 of the sizer 30. While the sizer 30 could be loaded from either side, it can only be loaded onto the sizer coupler 28 in one orientation, with the sizer catch placed within the first inner clearance gap 54 with the latch 50 and retainer 46 on the inner portion of the sizer catch 34 of the mounting feature 32 as shown in FIG. 5A. This described configuration and interlocking and complementary features on the sizer coupler 28 and sizer 30 are advantageous in preventing or reducing the possibility of misplacing or loading a sizer 30 onto the sizer sound 10 in a manner that would prevent the instrument from operating correctly or having a sizer become inadvertently dislodged.

FIGS. 7A-7E are side, partial cross-sectional views of the surgical sizer sound of FIG. 1 during a surgical procedure introducing the surgical sizer sound between two ribs. An over all microthoracotomy may consist of several general steps, only some of which, relevant to a sizer sound device, are described herein. Once access for a microthoracotomy is established, typically via at least one small incision wherein a scope port or other access port is established, cardiopulmonary bypass is also established. Aortic cross clamping, aortotomy, and aortic valve debridement and optional stabilization are subsequently conducted. Annular sizing is commonly a next step in a minimally invasive valve replacement procedure. The surgical sizer sound is introduced intercostally while actuating the surgical sizer sound to minimize interference with one or more ribs. The surgical sizer sound is then advanced such that the sound attachment is inserted into the appropriate annulus which is the target site of the valve replacement. The sizer and successively larger sizers are inserted into the annulus until an adequate and complete fit of the largest possible sizer is determined. This size is used as the optimal valve size choice. A replica attachment may also be attached to the sizer coupler where applicable to verify the correct valve size. FIG. 7A is a side view partial cross-section of an internal view of an intercostal space surrounded by two ribs 72, 74, which is a typical insertion point for a sizer sound 10 such as the one described herein. Usually a minimally invasive surgical procedure involving a microthoracotomy utilizes either the second or third intercostal space between the ribs. The orientation of the sizer coupler 28 relative to the angled shaft 26 is shown here as neutral, although any angle of the sizer coupler 28 relative to the angled shaft 26 could be utilized based on present surgical conditions and preference of the surgeon. The sizer 30 is loaded onto the sizer coupler 28 as previously described herein. The sizer is placed between rib 72 and rib 74 and guided therethrough by the sizer sound 10. In some instances, although not shown here, rib retractors or other means may be used to further separate the ribs 72, 74 to gain increased intercostal space. FIG. 7B illustrates the sizer 30 being advanced further into the intercostal space between the ribs 72, 74, guided by the sizer sound 10. As the sizer sound 10 and more specifically the sizer coupler 28 interferes with rib 72, it is necessary to further angulate the distal end 10D of the sizer sound 10 in a manner that allows the sizer 30 to be further advanced atraumatically through the intercostal space. Further angulation and positioning of the sizer 30 may be necessary, as shown in FIG. 7C, which may be achieved via rotation or angulation of the entire sizer sound 10, as well as by articulating the sizer coupler 28 portion of the device relative to the angled shaft 26. The sizer 30 is in a position to be further guided around the ribs 72, 74 on a continuing atraumatic path towards the heart. FIG. 7D illustrates the sizer 30 having passed mostly through the intercostal space between the ribs 72, 74 and finally passed entirely through the intercostal space, as illustrated in FIG. 7E. Subsequently, the sizer 30 may be advanced, angled, and articulated as necessary to place the sizer 30 within the aortic annulus, in the case of an aortic valve replacement, for proper sizing and fit of the annulus for the purpose of utilizing the most appropriately sized replacement valve for the individual anatomical considerations of the patient.

Figure 8:
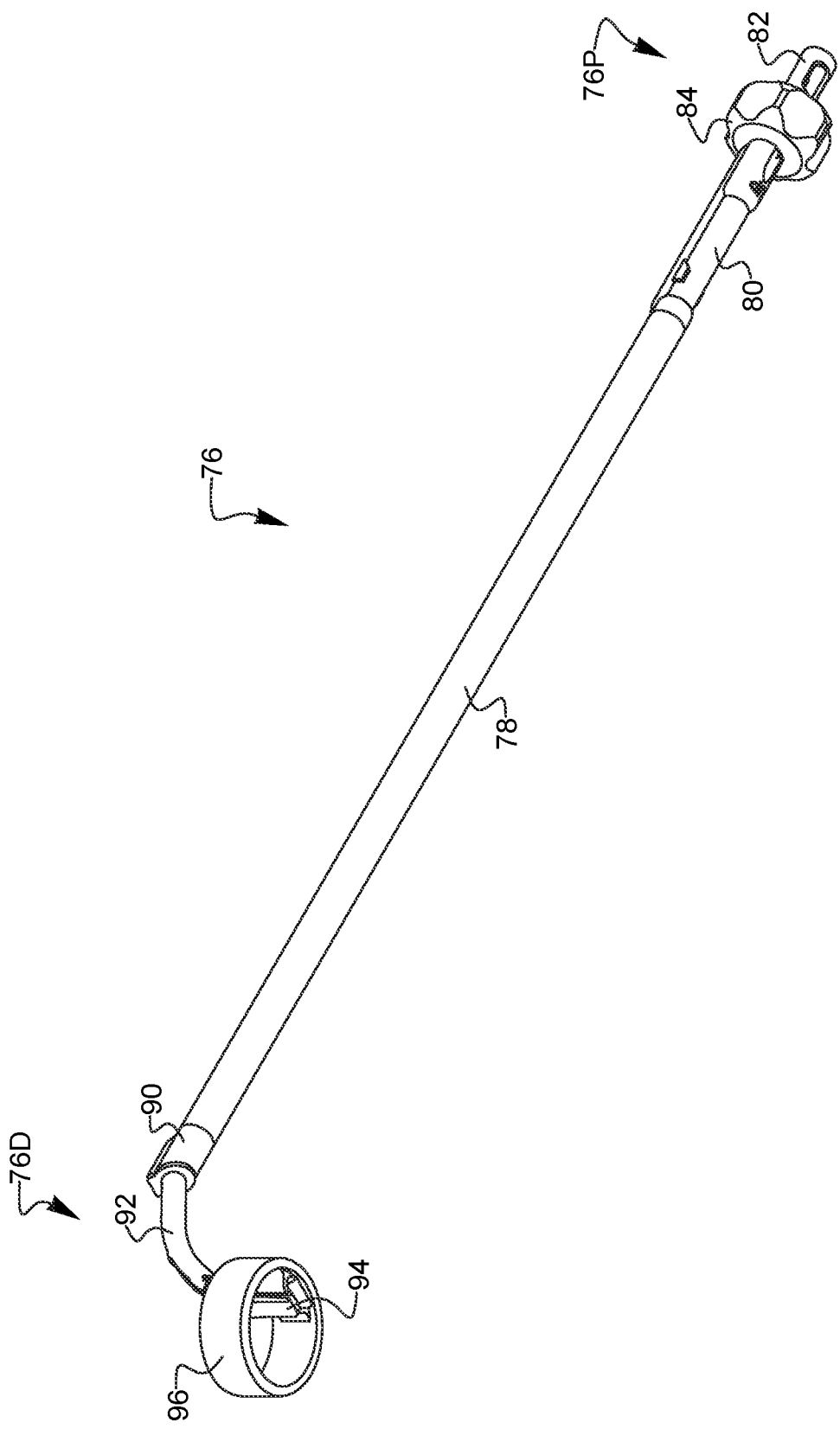
FIG. 8 is a bottom front left perspective view of an alternate embodiment of a surgical sizer sound.

FIG. 8 is a bottom front left perspective view of an alternate embodiment of a surgical sizer sound. A sizer sound 76 having a guide shaft 78 with an angled shat mount 90 disposed towards the distal end 76D of the sizer sound 76, the angled shaft mount 90 coupled to an angled shaft 92. Similar to previous embodiments, the sizer sound 76 includes a sizer coupler 94 pivotably coupled to the angled shaft 92. A sizer 96 is releasably coupled to the sizer coupler 94 on the distal end 76D. A handle 80 is coupled to the guide shaft 78, and a rotating knob 84 and an end cap 82 are also disposed at a proximal end 76P of the sound 76. The knob 84 shown in FIG. 8 has a more ergonomic design for improved handling and grip. The operating principles and internal components of this embodiment of a sizer sound 76 are similar to that of the embodiment illustrated in FIG. 1 and described previously herein.

Various advantages of a surgical sizer sound have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical sizer sound, comprising:
    an actuatable shaft that extends from a proximal end of the actuatable shaft to a distal end of the actuatable shaft;
    a rotational knob coupled to the actuatable shaft, wherein the rotational knob is configured to displace in a first knob direction relative to the distal end of the actuatable shaft and a second knob direction relative to the distal end of the actuatable shaft;
    an angled shaft that extends from a proximal end of the angled shaft to a distal end of the angled shaft, wherein the proximal end of the angled shaft is coupled to the distal end of the actuatable shaft;
    a drive wire that extends from a proximal end to a distal end, wherein the proximal end of the drive wire is coupled to a portion of the rotational knob, and wherein a first portion of the drive wire is disposed within an interior portion of the actuatable shaft;
    a sizer coupler, having a first portion that is pivotably coupled to a portion of the angled shaft that is disposed at the distal end of the angled shaft, the sizer coupler having a second portion coupled to the distal end of the drive wire, and the sizer coupler having a third portion comprising:
        an elongated guide tip that extends from a first end of the guide tip to a second end of the guide tip along a guide tip axis, and wherein the guide tip axis is linear;
        an elongated retainer that extends from a first end of the retainer to a second end of the retainer along a retainer axis that is linear, wherein a latch is formed at the second end of the retainer, the latch extending from a first surface in a first retainer direction normal to the retainer axis and towards the guide tip;
        a biasing element that extends from the first end of the retainer to a first portion of the guide tip, wherein a first portion of the biasing element extends from the first end of the retainer to an intermediate point and a second portion of the biasing element extends from the intermediate point to the first portion of the guide tip, the first portion of the biasing element extending along a first portion axis that is curved, and wherein the second end of the retainer is displaceable relative to the second end of the guide tip along an axis that is normal to the retainer axis; and
        an elongated limit member that extends from a first end to a second end along a limit member axis, wherein the retainer is disposed between the guide tip and the limit member such that the first surface of the retainer faces the guide tip and a second surface of the retainer faces a portion of the limit member, and wherein a portion of the second surface of the retainer is configured to contact the portion of the limit member when the retainer displaces in a second retainer direction normal to the retainer axis, thereby limiting the displacement of the retainer relative to the limit member in the second retainer direction; and
    a sizer comprising a sizing portion and a mounting portion, the sizing portion comprising a cylindrical body, the mounting portion being disposed along a portion of the cylindrical body, the mounting portion including a slot that is adapted to removably receive at least a second portion of the guide tip such that the latch of the retainer operatively engages an edge portion of a wall that at least partially defines the slot to releasably secure the sizer coupler to the sizer,
    wherein (a) when the rotational knob is displaced in the first knob direction, the distal end of the drive wire displaces distally, causing the sizer coupler and the sizer to pivot about an axis extending through the first portion of the sizer coupler in a first rotational direction, and
    (b) when the rotational knob is displaced in the second knob direction, the distal end of the drive wire displaces proximally, causing the sizer coupler and the sizer to pivot about the axis extending through the first portion of the sizer coupler in a second rotational direction.

2. The surgical sizer sound of claim 1, wherein the sizer coupler further comprises a stop.

3. The surgical sizer sound of claim 1, wherein the sizer coupler is formed of a singular piece.

4. The surgical sizer sound of claim 1, wherein the angled shaft is articulable.

5. The surgical sizer sound of claim 1, wherein a second portion of the drive wire is disposed within an interior portion of the angled shaft.

6. The surgical sizer sound of claim 1, wherein the rotational knob is configured to rotate in (a) a first knob rotational direction to distally displace relative to the distal end of the actuatable shaft and (b) a second knob rotational direction to proximally displace relative to the distal end of the actuatable shaft.

7. The surgical sizer sound of claim 1, wherein the rotational knob is disposed at or adjacent to the proximal end of the actuatable shaft.

8. The surgical sizer sound of claim 1, wherein the second end of the guide tip is aligned with the second end of the retainer along an axis that is normal to the guide tip axis.

9. The surgical sizer sound of claim 1, wherein the guide tip axis is parallel to the retainer axis.

10. The surgical sizer sound of claim 1, wherein the second portion of the biasing element extends along a second portion axis that is linear.

11. The surgical sizer sound of claim 10, wherein the intermediate point is aligned with the first end of the retainer along an axis that is normal to the retainer axis.

12. The surgical sizer sound of claim 10, wherein the first portion axis has a shape of a segment of a circle.

\* \* \* \* \*